United States Patent [19]
Cserfalvi et al.

[11] Patent Number: 5,760,897
[45] Date of Patent: Jun. 2, 1998

[54] PROCESS FOR ATOMISING ELECTROLYTES AND THE CHEMICAL ANALYSIS THEREOF

[75] Inventors: Tamas Cserfalvi; Pal Mezei, both of Budapest, Hungary

[73] Assignee: Aqua-Concorde KFT, Budapest, Hungary

[21] Appl. No.: 569,153

[22] PCT Filed: Jun. 23, 1994

[86] PCT No.: PCT/HU94/00021

§ 371 Date: Apr. 15, 1996

§ 102(e) Date: Apr. 15, 1996

[87] PCT Pub. No.: WO95/01562

PCT Pub. Date: Jan. 12, 1995

[30] Foreign Application Priority Data

Jun. 23, 1993 [HU] Hungary ................... 93 01849

[51] Int. Cl.[6] ................................................. G01N 21/67
[52] U.S. Cl. ................................................. 356/313
[58] Field of Search ............................. 356/311, 313

[56] References Cited

U.S. PATENT DOCUMENTS

| 2,643,574 | 6/1953 | Todd | 356/313 |
| 4,195,641 | 4/1980 | Joines et al. | 356/311 |

FOREIGN PATENT DOCUMENTS

| 231752 | 2/1964 | Austria . |
| WO 86/01892 | 3/1986 | WIPO . |
| WO 93/01486 | 1/1993 | WIPO . |

*Primary Examiner*—F. L. Evans
*Attorney, Agent, or Firm*—Morrison & Foerster LLP

[57] ABSTRACT

The present invention relates to a one-step process useful in the chemical analysis for atomising electrolyte solutions or fluids with electric conductivity, and a multielement direct analysis method of the components of such fluids, which is also operable in a monitoring mode. In this analysis method, the one-step atomisation of the fluid is followed by optical and/or mass spectroscopy determination of the sample components. The atomisation process is characterised by generating an electric discharge of 1000 to 5000 V/cm on the surface of said electrolyte between the fluid as cathode and the anode positioned in the gas atmosphere above the said fluid.

19 Claims, 2 Drawing Sheets

PROCESS FOR ATOMISING ELECTROLYTES AND THE CHEMICAL ANALYSIS THEREOF

TECHNICAL FIELD

The present invention relates to a one-step process useful in the chemical analysis for atomising electrolyte solutions or fluids with electric conductivity, and a multielement direct analysis method of the components of such fluids, which is also operable in a monitoring mode. In this analysis method, the one-step atomisation of the fluid is followed by optical and/or mass spectroscopy determination of the sample components.

BACKGROUND ART

In many fields of optical spectroscopy (atomic absorption or atomic emission spectrophotometry, atomic fluorescence) and mass spectroscopy the precondition of measurement is the existence of the components in an atomic vapour state. The term: "atomisation" defines a complex process wherein an atomic aerosol is obtained from the sample by one or multistep energy transfer. In the following, the term: "atomisation" is used in this sense.

According to the prior art, most of the atomisation processes used for analytical purposes prepares first a coarse aerosol by pneumatic vaporisation of the electrolyte solution, which is then transferred into properly selected chemical flame of high temperature or plasma flame generated by high frequency (Boumans, editor: Theory of Atomic Emission Spectroscopy). In these processes the vaporisation step, due to the small sample requirement, is performed by capillary blotting or blow-slot method and accordingly, they can be used in the analysis of solutions which are predominantly clear and/or contain little amount of floating material, which would mean the necessity of inserting a pre-filtering step before vaporisation in many practical processes. The mass flow of atomisation, i.e. the amount of electrolyte atomised in a time unit is determined by the atomisation velocity, thus, regular cleaning of the vaporisation system and permanent control of the flow and pressure conditions is necessary. Another drawback of such processes is that atomisation by chemical flames needs a permanent and strict control due to the extraordinarily flammable and explosive gases (acetylene, dinitrogen oxide, oxygen) used therein. This disadvantage does not appear in the high frequency-generated plasma flame atomisation, but the high frequency unit is of complicated structure and high energy consumption.

Another method for solution atomisation used for analytical purposes is the electro-thermal, heating of a precisely determined quantity of electrolyte by programmed steps of evaporation, drying and vaporisation, the so-called graphite furnace atomisation. This method provides an advantageous high atom vapour concentration, however, the process is complicated and consists of multiple steps, automation of sample injection is difficult to accomplish, and continuous working mode is impossible due to permanent contamination of the graphite furnace by the non-evaporating parts of the electrolytes.

In the optical spectroscopy, other methods for quasi-continuous atomisation and analysis connected therewith in dude "weeping carbon electrode" method (Feldman, C.: Anal. Chem. 21: 1041/1949/), "capillary electrode carbon arc" method (Nalimov, V. V.: Zav. Lab. 23: 1351/1955/, Zink, T. H. Appl. Spectr. 13: 94/1959/), rotating disc electrode spark excitation (Pierucci, M. et al: Nuovo Cimento 17: 275/1931/) and feeding electrolyte in the spark gap (Twyman, F. et al: Proc. Roy. Soc. 133: 72/1931/). These methods have never been widely used due to their common disadvantage that during atomisation, irreversible deposits are formed on the solid electrodes, and accordingly, they cannot be used in continuous technologies.

As summarized above, the known analytical methods based on analytical chemical atomisation processes of electrolyte-containing fluids (atomic absorption, atomic emission, atomic fluorescence, mass spectroscopy) require a very thorough sample preparation, (filtration, recovery, dissolving), precise solution administration, permanent control (explosion risk in technology) and they are not suitable for continuous, control-free (monitoring) system.

Accordingly, the present application aims to provide a one-step method for atomising electrolyte solutions and an atomic spectroscopy based thereon for a multielement analysis, which eliminate the above disadvantages.

DISCLOSURE OF THE INVENTION

The invention is based on the recognition, that atomisation of an electrolyte may be carried out by generating an electric gas discharge of 1000 to 5000 V/cm intensity on the surface of the electrolyte between the fluid as cathode and an anode arranged in the atmosphere above the electrolyte. It has been found that as an embodiment, the following method is suitable for one-step direct multielement analysis:

The pH-value of the fluids is optionally adjusted to acidic, preferably in the interval of 1.0 to 2.0, a part of the fluid is atomised by generating electric gas discharge on the surface of fluid between the electrolyte as cathode and the anode arranged in the gas atmosphere above the electrolyte, and the constitution of the sample is determined by methods known per se, by optical spectrometry based on light emission created by excitation of the atomic vapours obtained from the components, or by direct mass spectrometric analysis of the atomic vapours.

It has also been found that the presence of an extremely high amount of alkali earth metal in the sample (10 to 100 g/l) can substitute the acidifying step, and by using the above electrode arrangement and field strength interval, both the atomisation and the analysis connected therewith can be carried out.

According to a preferred embodiment of the invention the atomisation of the electrolytes can be carried out by generating a direct current gas discharge of a field strength from 1000 to 5000 V/cm on the fluid surface between the electrolyte as cathode and the anode positioned in the vapour atmosphere above the electrolyte. The field strength can be controlled by the voltage and the distance between the electrode. The atomisation mass flow, i.e. the quantity of the sample atomised and entering the plasma in a time unit reaches a defined, constant value by adjusting the field strength and the current rate to a constant value, and thus, sample administration becomes superfluous.

In the gas discharge process, only atomisation of the cathode takes place; the anode serves for conducting away the electrons formed in the discharging process (G. Francis: Glow Discharges at Low Pressures, Handbuch der Physik Vol. XXII, Springer V. Berlin 1956). Thus the material of anode does not disturb the process provided that it is sufficiently heat-resistant.

BEST MODE OF CARRYING OUT THE INVENTION

Figure 1:
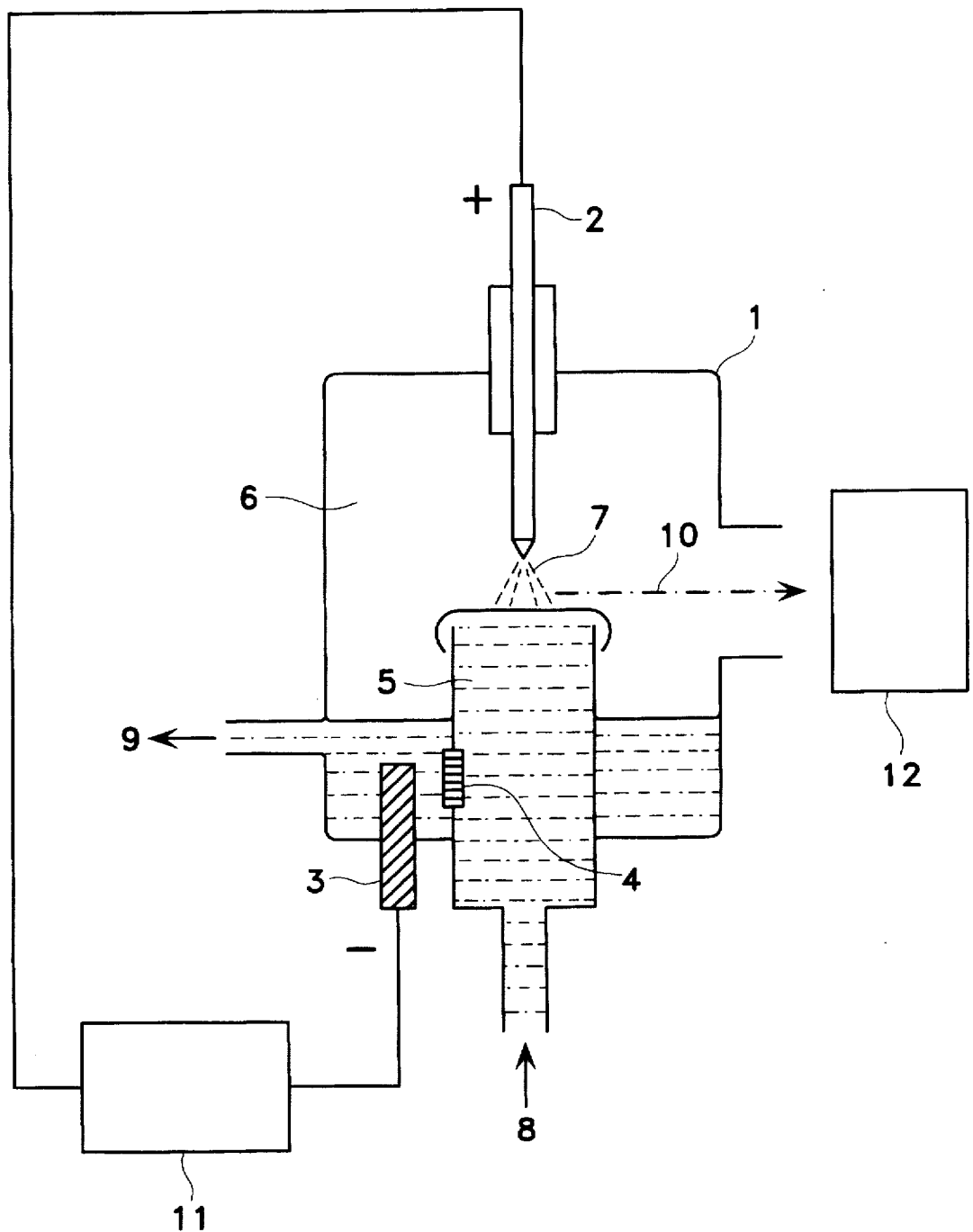
FIG. 1 shows a possible embodiment of the atomisation.

A possible embodiment of the atomisation is shown in FIG. 1. In the discharge cell made of a non-conducting material (glass) (1) a heat-resistant anode electrode (Tungsten) (2) is inserted to a distance of 3 to 6 mm above the surface of the electrolyte cathode (5). The electrolyte cathode (5) is in electric contact with the electrode (3) via the diaphragm (4). The electrode (3) is placed in the pole space of the effluent electrolyte (9). The electrode (3) is connected with the negative pole of a high voltage power supply, while the electrode (2) is connected to the positive pole thereof. The light emission of the discharge plasma (7) forming in the gas region (6) is detected by an optical spectrometer (12) directed in the observation direction (10). The sample is fed into the cathode space. (5) through the connection (8).

The atomisation can be carried out by single sample injection or during flow of the fluid containing the electrolyte. Flow of the solution containing the electrolyte in the gas discharge pole space is especially preferred as the flow of fluid can also be used for heat transfer. In the single sample injection mode, cooling can be accomplished e.g. in a cell with coolant jacket.

The preparatory process of the electrolyte solutions for analysis occasionally needs a pretreatment step. If the sample is a dilute solution, pretreatment constitutes adjustment of the pH value, which is accomplished suitably with mineral acids, preferably to a pH value of 1.0 to 2.0. Control of the adjustment in a static or dynamic system may be carried out in methods known per se, e.g. by pH measurement.

Should the sample contain the alkali and alkali earth metal salts in a higher concentration, e.g. 10 to 100 g/l, acidification may be omitted.

In one embodiment, wherein the electrolyte solution contains less than 2 g/l alkali metal and alkali earth metal ions, the pH of the electrolyte solution is adjusted to a value of 0.5 to 3, preferably to a value of 1 to 2, by the addition of an acid. In one embodiment, wherein the electrolyte fluid contains from 2 to 10 g/l alkali metal and alkali earth metal ions, the pH of the electrolyte solution is adjusted to a value of 3 to 5 by the addition of an acid.

The gas plasma atomised according to the invention excites a part of the components of the atomic vapour to light emission. This light radiation forms the basis of the optical spectroscopy analysis. Accordingly, the intensity of light radiation emitted by the excited components of electrolyte solutions induced by one-step atomisation, such as metal atoms, can be determined by direct optical spectroscopy methods, which provides signals having intensity proportional with the concentration of a component at a wave length characteristic to each component. The non-excited components can be analysed by directing them out of the atomised gas atmosphere, e.g. by vacuum, and by mass spectroscopy methods known per se.

The interfering background radiations known from optical emission spectroscopy (e.g. the bands of radicals formed from the solvent and the components of the gas atmosphere, resp.), are also present in the emission spectrum of the plasma atomised according to the invention, and, in certain ranges, they substantially reduce the accuracy of the analytical measurement by increasing the background noise.

It has also been found that the band radiation of the atomized gas plasma molecules and radicals according to the invention can substantially be reduced periodically by using additive current impulse. The direction of the applicable current impulse is identical with that of the discharge supporting current, its strength is 2 to 10 times higher, the term is 100 to 1000 microseconds, the upper limit of the duty cycle is about 20%, i.e. 1 to 4 pulse:interval ratio.

The intensity of the light emitted should suitably be determined in the second half of the current pulse, or in the term 10 to 100 microseconds after the end of the current pulse, wherein the intensity of the background signal decreased to a low level, or, in the latter case approached or reached the dark current level of the detector.

Figure 2:
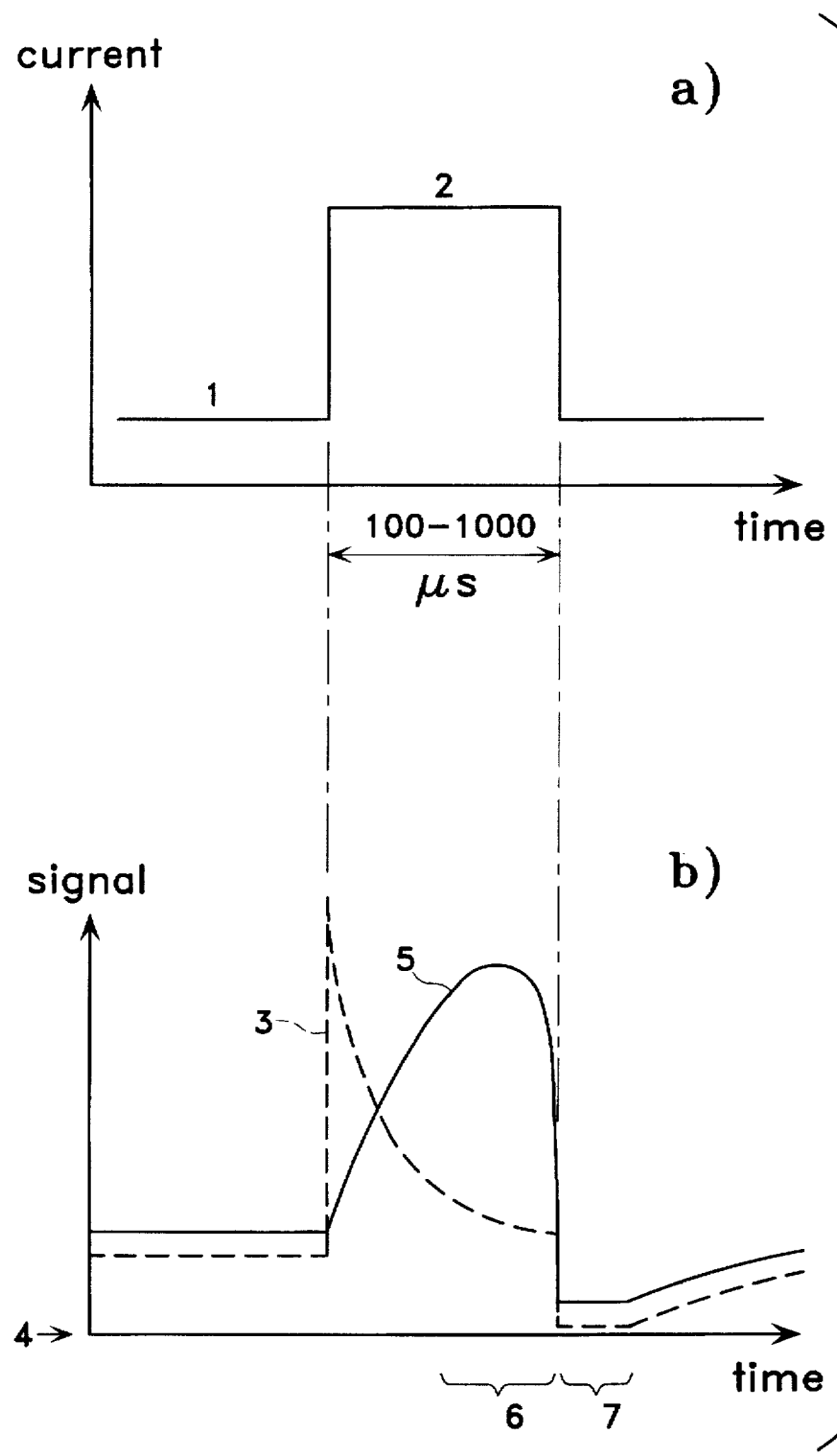
FIG. 2 shows a preferred embodiment of the pulse generation and time resolution measurement

A preferred embodiment of the pulse generation and time resolved measurement is shown in FIG. 2. A section of the field current increased during one pulse is illustrated in FIG. 2a. On the basic discharge current (1) a current pulse (2) of 100 to 1000 microseconds is superimposed. FIG. 2b shows the concurrently registrable detector signal function. Curve 3 corresponds to the intensity of the band background radiation, curve 5 is a typical example of the atomic line intensity during the current pulse and closely before and after thereof. The line intensity (5) measured during the interval (6), was improved to 2 to 5-fold of the signal/background ratio (compared to background 3) and 2 to 10-fold of the pulseless direct current excitation. The term (7) is a background decay period after the current impulse (2), wherein the intensity of plasma emission might decrease almost to zero.

The pulse excitation and time resolved measurement method according to the invention can be evaluated with a calibration curve taken between the signal intensity during the time intervals 6 or 7 on a wavelength characteristic to the target component and the concentration of said component.

The possibility of continuous sample feeding constitutes one of the greatest advantages of the present invention, as the method can be used in complex industrial and environmental monitoring systems. A further great advantage of the multielement analysis according to the invention is that the known processes are substantially simplified by eliminating the preparation of samples through controlled mass flow direct atomisation, i.e., without pulverisation, drying and thermal vaporisation.

In the process according to the invention the atomisation mass flow is 1 to 2 orders of magnitude smaller than that of known atomisation processes, and accordingly, the sensitivity of the method is at least one order of magnitude less than that of the laboratory atomic spectroscopy methods. However, this sensitivity of the analytical method according to the invention is suitable in most of the industrial, environmental, etc., analytical processes.

The progressive effects of the invention can be summarised as follows:

one-step, direct atomisation by atomisation mass flow controlled by the field strength and discharge current strength, the atomisation takes place on the free fluid surface of the sample flow, a permanently recovering surface is formed, i.e. the sample preparatory line needs not more than an eventual crude filtration, a steady state is formed by permanent ventilation of the recovering fluid surface and the gas space, as well as the heat removal, i.e. there is no deposition surface, and atomisation process can be maintained continuously as well.

We claim:

1. A method for atomizing an electrolyte fluid, said method comprising the step of generating a gas discharge by providing a field strength of 1000 to 5000 V/cm between a surface of said electrolyte fluid, as cathode, and an electrode, as anode, positioned in an atmosphere above said surface.

2. The method of claim 1, wherein said electrode, as anode, is a heat resistant material.

3. The method of claim 1, wherein said electrode, as anode, is positioned 3 to 6 mm above said surface.

4. The method of claim 1, wherein said electrolyte fluid, as cathode, is an electrolyte solution.

5. A method for elemental analysis of electrolyte fluid, said method comprising the steps of:
   (a) generating a gas discharge by providing a field strength of 1000 to 5000 V/cm between a surface of said electrolyte fluid, as cathode, and an electrode, as anode, positioned in an atmosphere above said surface; and
   (b) determining the elemental constitution of said gas discharge.

6. The method of claim 5, wherein said elemental constitution of said gas discharge is determined by optical spectrometry.

7. The method of claim 5, wherein said elemental constitution of said gas discharge is determined by mass spectrometry.

8. The method of claim 5, wherein said electrode, as anode, is a heat resistant material.

9. The method of claim 5, wherein said electrode, as anode, is positioned 3 to 6 mm above said surface.

10. The method of claim 5, wherein said electrolyte fluid, as cathode, is an electrolyte solution.

11. The method of claim 5, wherein said electrolyte fluid contains less than 2 g/l alkali metal and alkali earth metal ions, and the pH of said electrolyte fluid is adjusted to be from 0.5 to 3.

12. The method of claim 5, wherein said electrolyte fluid contains less than 2 g/l alkali metal and alkali earth metal ions, and the pH of said electrolyte fluid is adjusted to be from 1 to 2.

13. The method of claim 11, wherein the pH of said electrolyte fluid is adjusted by the addition of a mineral acid.

14. The method of claim 5, wherein said electrolyte fluid contains from 2 to 10 g/l alkali metal and alkali earth metal ions, and the pH of said electrolyte fluid is adjusted to be from 3 to 5.

15. The method of claim 14, wherein the pH of said electrolyte fluid is adjusted by the addition of a mineral acid.

16. The method of claim 5, wherein said field strength is provided by applying a current comprised of current pulses superimposed on a base current of the same sign.

17. The method of claim 16, wherein said current pulses have an intensity 2 to 10 times greater than the intensity of said base current, a term of 100 to 1000 microseconds and a maximum duty cycle of 20%.

18. The method of claim 17, wherein the elemental constitution of said gas discharge is determined during the latter half of said current pulse term.

19. The method of claim 17, wherein the elemental constitution of said gas discharge is determined 10 to 100 microseconds after said current pulse term.

* * * * *